US011395766B2

(12) United States Patent
Leppänen et al.

(10) Patent No.: US 11,395,766 B2
(45) Date of Patent: Jul. 26, 2022

(54) MEDICAL DRESSING FOR A CONVEX BODY PART

(71) Applicant: Mölnlycke Health Care AB, Gothenburg (SE)

(72) Inventors: Timo Leppänen, Klippan (SE); Karin Östan, Nödinge (SE); Patrick Rodzewicz, Gothenburg (SE); Malin Mårtensson, Borås (SE)

(73) Assignee: Mölnlycke Health Care AB, Gothenburg (SE)

( * ) Notice: Subject to any disclaimer, the term of this patent is extended or adjusted under 35 U.S.C. 154(b) by 580 days.

(21) Appl. No.: 16/467,517

(22) PCT Filed: Jan. 10, 2018

(86) PCT No.: PCT/EP2018/050547
§ 371 (c)(1),
(2) Date: Jun. 7, 2019

(87) PCT Pub. No.: WO2018/130562
PCT Pub. Date: Jul. 19, 2018

(65) Prior Publication Data
US 2019/0328579 A1    Oct. 31, 2019

(30) Foreign Application Priority Data

Jan. 11, 2017  (EP) .................................... 17151011

(51) Int. Cl.
*A61F 13/00* (2006.01)
*A61F 13/02* (2006.01)
(Continued)

(52) U.S. Cl.
CPC ............ *A61F 13/00* (2013.01); *A61F 13/025* (2013.01); *A61F 13/0266* (2013.01);
(Continued)

(58) Field of Classification Search
CPC .... A61F 13/00; A61F 13/025; A61F 13/0266; A61F 13/0289; A61F 13/061;
(Continued)

(56) References Cited

U.S. PATENT DOCUMENTS 5,827,213 A * 10/1998 Jensen .................. A61F 13/101
602/62

FOREIGN PATENT DOCUMENTS

EP    0768071 A1    4/1997
EP    0769283 A1    4/1997
(Continued)

OTHER PUBLICATIONS

International Search Report and Written Opinion dated Feb. 14, 2018 by the International Searching Authority for Patent Application No. PCT/EP2018/050547, which was filed on Jan. 10, 2018 and published as WO 2018/130562 on Jul. 19, 2018 (Inventor—Leppanen et al.; Applicant—Molnlycke Health Care AB) (13 pages).

*Primary Examiner* — Ophelia A Hawthorne
(74) *Attorney, Agent, or Firm* — Ballard Spahr LLP

(57) ABSTRACT

Disclosed is a medical dressing having a pad and a border portion. The pad can have a rim and the border portion extends along said rim. The medical dressing can be arranged in a first substantially planar configuration and be folded along a first line, and a second portion of said medical dressing is formed and a second substantially cup-shaped configuration. The first portion can be facing and contacting said second portion. Said first substantially planar configuration the first and second portions can be connected by means of a fixed connection along a second line, which defines a second line segment having a first and a second end-point. The first and second line segments are connected at their respective first end-points such that an angle between 90 and 175 degrees is formed between the first and second (Continued)

line segments when the medical dressing is in the first substantially planar configuration.

15 Claims, 6 Drawing Sheets

(51) Int. Cl.
*A61F 13/06* (2006.01)
*A61F 13/10* (2006.01)

(52) U.S. Cl.
CPC ........ *A61F 13/0289* (2013.01); *A61F 13/061* (2013.01); *A61F 13/064* (2013.01); *A61F 13/101* (2013.01); *A61F 2013/00578* (2013.01); *A61F 2013/00604* (2013.01)

(58) Field of Classification Search
CPC .................. A61F 13/064; A61F 13/101; A61F 2013/00578; A61F 2013/00604; A61F 13/023; A61F 2013/00817; A61F 13/00085; A61F 13/0269; A61F 15/004; A61F 2013/00536; A61F 2013/0054; A61F 2013/00646; A61F 2013/00812; A61F 2013/00574; A61F 13/066; A61F 2013/00868; A61F 5/0106; A61F 13/10
See application file for complete search history.

(56) References Cited

FOREIGN PATENT DOCUMENTS

| | | | |
|---|---|---|---|
| EP | 3023083 A1 | 5/2016 | |
| WO | WO-1992/005756 A1 | 4/1992 | |
| WO | WO-1993/019710 A1 | 10/1993 | |
| WO | WO-2008/149107 A1 | 12/2008 | |
| WO | WO-2013/001210 A1 | 1/2013 | |
| WO | WO-2013001210 A1 * | 1/2013 | ......... A61F 13/0206 |

* cited by examiner

MEDICAL DRESSING FOR A CONVEX BODY PART

CROSS-REFERENCE TO RELATED APPLICATIONS

This application is a U.S. National Phase Application of International Application No. PCT/EP2018/050547, filed Jan. 10, 2018, which claims priority to European Application No. 17151011.8, filed Jan. 11, 2017, each of which are hereby incorporated by reference in their entirety.

TECHNICAL FIELD

The present invention relates to a medical dressing for use on a convex body part and a method for providing such a medical dressing.

BACKGROUND

Medical dressings are often used for treatment of open wounds. The medical dressing shall for example absorb wound fluids that exit the wound and protect the wound from e.g. bacterial and viral infections. The medical dressing will hence be applied to the human body after such a wound has arisen. In addition, medical dressings may also be used proactively to prevent e.g. pressure ulcers to arise among persons being bedridden for various reason, for example due to long term hospitalization or other causes of immobility.

Convex body parts of the human body, such as heels and elbows, may cause problems when applying a medical dressing and they are therefore often referred to as "hard to dress-areas". Applying a dressing to e.g. a heel for wound treatment and/or for pressure ulcer preventing purposes may be challenging since it includes covering parts of the foot sole as well as the lateral and medial sides of the foot, resulting in numerous directions and planes of extensions for the dressing. Applying a dressing to another convex part of the human body, such as an elbow or a knee may be challenging for the same reasons. It is desired to have full coverage of such convex body parts since the convex body parts, such as the heel, comprise bony prominences where the skin is more vulnerable and therefore there is a higher risk for pressure ulcers to arise. Examples of such bony prominences of the heel is: under the heel, on the outside of the heel and the malleoli.

Two different types of medical dressings may be used for covering convex body parts, namely flat dressings and cup-shaped dressings. Two examples of cup-shaped dressing have been presented in WO92/05756 and WO2013/001210.

Flat dressings are typically difficult to apply correctly. The dressing must be folded to conform to the shape of the convex body part, and this results in overlap of the border portion of the dressing. This may impact the stay-on ability, especially if the skin needs to be checked and the dressing is detached and replaced several times. Also, there is a risk for forming gaps and/or folds when applying the medical dressing to a convex body part. Gaps may create unprotected spots, and pressure applied to those spots may increase the risk for a pressure ulcer to arise. For treatment purposes, a gap may further expose a wound for a higher risk for infection.

A problem with cup-shaped medical dressings is that they often come in one size which may not fit all convex body parts and not all patients since the anatomy differs from patient to patient. As the cup-size is often fixed, there is no possibility for adapting the cup for a certain convex body part or for a certain patient when applying the medical dressing. This increases the risk for folds to be created. Another problem with the cup-shaped dressings is that excess material of the cup tends to be gathered in the bottom of the cup-shaped medical dressing when it is applied to a patient. The excess material may be of discomfort for the patient, and the dressing may fall off. Cup-shaped medical dressings may also comprise high and sharp edges which may be of discomfort and may give rise to pressure ulcers.

SUMMARY OF THE INVENTION

It is an object of the present invention to improve the current state of the art and to mitigate at least some of the above mentioned problems. These, and other objects, are achieved by a medical dressing for use on a convex part of the human body and by a method for providing a medical dressing for a convex part of the body.

According to a first aspect of the present invention a medical dressing for use on a convex part of the human body is provided. Said medical dressing comprises a pad and a border portion;
wherein said pad comprises a rim and said border portion extends along said rim (suitably along the entire rim) and comprises an adhesive body contact layer; and
wherein said medical dressing can be arranged in a first substantially planar configuration and a second substantially cup-shaped configuration;
wherein in said first substantially planar configuration:
said medical dressing is folded along a first line defining a first line segment having a first and a second end-point such that a first portion and a second portion of said medical dressing is formed, wherein said first portion of said medical dressing is facing and contacting said second portion of said medical dressing;
said first and second portions of said medical dressing are connected by means of a fixed connection along a second line defining a second line segment having a first and a second end-point;
said first and second line segments being connected at their respective first end-points such that an angle between 90 and 175 degrees or preferably between 120-170 degrees, or more preferably between 140-160 degrees, is formed between said first and second line segments;
wherein in said second substantially cup-shaped configuration:
said border portion forms a peripheral edge of said medical dressing; and
said second end-points of said first and second line segments lay on said peripheral edge of said medical dressing.

The present invention is based on the realization that by providing a medical dressing having a second substantially cup-shaped configuration, the arrangement of the medical dressing on a convex part of a human body is facilitated. The dressing adopts a semi 3D shape that resembles the contour of the human body. By providing the medical dressing with a fold as a first line segment, the size and shape of the cup and hence the dimensions of the medical dressing can more easily be adapted to the patient, thereby lowering the risk of folds or gathering of material, which is an advantage in relation to previously known cup-shaped dressings of a fixed size. Folds created when applying the medical dressing to e.g. a heel may be perceived by the patient as a sharp edge against the skin. Such a sharp edge may chafe the skin and hence they may provide a larger risk for developing pressure ulcers. Furthermore, as the first and second portions are connected to each other by a fixed connection the risk of gaps formed during application of the medical dressing is reduced as compared to previously known flat medical dressings. Such gaps may be of great discomfort for the person wearing the medical dressing. For example, gaps may create unprotected spots and pressure applied to such spots may give rise to pressure ulcers. Furthermore, when using the medical dressing for prevention of pressure ulcer, the preventing capacity of the medical dressing may be reduced. When using the medical dressing for wound treatment, gaps increase the risk for infection and leakage of wound fluids.

Each of the layers of the medical dressing is made integral where the fold which defines the first and the second portion is made. In other words, the first and second portions are connected to each other at least along a part of each layer of the medical dressing. The fold may be provided at such a part and the fixed connection may be provided at a part where the different portions are not connected. Hence, there will not be any seams or edges on the surface of the part of the pad that is already connected. Such seams and/or edges may be uncomfortable for a patient wearing the medical dressing and may also reduce the adjustability of the dressing.

The angle formed by the first and second line segments decides the depth or the width of the "cup". For example, if the angle is closer to 175 degrees the cup will be shallower as compared with if the angle is closer to 90 degrees. It may be desirable to provide medical dressings with different angles, to provide different sizes of the cup such that it better fits different convex parts of human bodies such as, for example, a heel, an elbow, or a knee. Moreover, the size of the convex part may vary between different patients of the medical dressing.

It shall be understood that the rim of the pad is the edge of the pad. It does not need to be of a certain height or be an edge which raises a certain distance from the border portion.

The adhesive body contact layer of the border portion is provided on the inside of the cup when the medical dressing is in its cup-shaped configuration. The inside of the cup is the body-facing side of the medical dressing when the medical dressing is in use. By this adhesive body contact layer, the medical dressing may be applied to the body of a patient without the need for any additional fastening means such as e.g. bandages or socks. This is advantageous as it is more easy to apply the medical dressing if no additional fastening means must be employed.

According to at least one example embodiment of the present invention the rim of the pad may be beveled or slanted relative the surface of the pad. With such a configuration the height difference between the pad and the border portion is gradually increasing/decreasing and the provision of a sharp edge of the pad is avoided. Hence, there will not be such a sharp edge that risks chafing the patient's skin and a medical dressing which is more comfortable for the patient is thereby provided.

According to at least one example embodiment of the present invention the pad can be provided in different shapes. For example, the pad may be a square, or it may be circular or elliptic, or it may be in the form of a butterfly. Moreover, it may be of any irregular shape. The desired shape of the pad may depend on the intended use of the medical dressing, i.e. for which convex part of the human body the medical dressing is intended.

According to at least one example embodiment of the present invention the width of border portion may vary along the rim of the pad. For example, the width of the border portion may vary between 5 mm and 70 mm, or it may vary between 10 mm and 45 mm. According to another example embodiment of the present invention the width of the border is constant along the rim of the pad.

According to at least one example embodiment the border portion extends along the entire rim of the pad such that the rim of the pad is surrounded/enclosed by the border portion.

According to at least one example embodiment of the present invention the second line segment may be straight or linear. A straight or linear second line segment may facilitate the manufacturing of the medical dressing.

According to at least another example embodiment of the present invention the second line segment may be non-linear. Moreover, the first portion and the second portion of the medical dressing may be connected by means of a fixed connection, which fixed connection is along a bended line. A bended line may conform better to the anatomy of the body part and may provide a different cup-shape, and hence, providing a bended line will affect the dimensions of the medical dressing. This provides a medical dressing which may be used on a different convex part of a human body and/or different patients.

In embodiments where the second line segment is non-linear, such as bended, the angle between the first and second line segments is to be measured in relation to a straight line extending between the first and second end point of the second line segment.

According to at least one example embodiment of the invention said pad comprises an indentation, and wherein said fixed connection of the medical dressing is provided in said indentation.

Providing an indentation in the pad, and providing the fixed connection in said indentation has several advantages. One advantage is that by providing the pad with an indentation less material will be used for the pad and the risk for excess material gathering is reduced. Without having an indentation, material from the pad may be gathered for example under the heel when the medical dressing is in use. Such gathered material may cause the patient discomfort and may chafe the patient's skin. In other words, a smoother inner surface of the medical dressing when arranged in the second substantially cup-shaped configuration may be provided when the pad comprises an indentation. Another advantage is that manufacturing is simplified when the fixed connection does not have to be provided through the pad. Even if it is possible to provide a fixed connection through certain types of pad materials, there is less limitations in choosing material for the pad if the fixed connection instead is provided in the indentation.

The length of the indentation, and thereby the possible length of the fixed connection affects the cup-shape of the medical dressing. Providing medical dressings with different lengths of the indentations may therefore be beneficial in order to provide medical dressings that fit different patients and different convex body parts.

According to at least one example embodiment the fixed connection is provided such that the edges of the opposite sides of the indentation are brought closer to each other by the fixed connection. By bringing the opposite sides of the indentation closer together, a cup-shape of the medical dressing is formed.

According to at least one example of the present invention opposite sides of the indentation is brought closer to each other such that the rim of the pad on both sides of the indentation are adjacent each other. When the rim of the pad on both sides of the indentation are adjacent each other, the risk of unintentionally providing areas of a patient's body that is not covered by the pad is lowered. Hence, the risk for gaps is reduced. Furthermore, in this embodiment, also the width of the indentation affects the cup-shape of the medical dressing. Providing medical dressings with different widths of the indentations may therefore be beneficial in order to provide medical dressings that fit different patients and different convex body parts.

According to at least one example embodiment of the present invention the ratio of the length of said first line segment and the length of said second line segment is 0.3-1.50, or more preferably 0.5-1. A ratio of 1 means that the first line segment and the second line segments is of equal length. A ratio of 0.5 means that the either the first line segment or the second line segment has a length that is twice the length of the other line segment. Moreover, the ratio of the length of the first and second line segments will affect the shape of the cup. Having one of the line segments longer than the other, i.e. a ratio below 1, will provide a shallower cup. By varying the ratio of the length of the first and the second line segment may provide a different shaped and sized medical dressing which may be suitable for different patients and/or different convex body parts, e.g. heels, knees or elbows.

When the dressing is to be applied to a heel, it may be advantageous that the length of the second line segment is longer than the length of the first line segment. For example, the ratio of the length between the first line segment and the length of the second line segment may be 0.4 to 0.8. This way, gathering of material under the heel (formed by a too long first line segment) is avoided.

According to at least one example embodiment of the present invention, in said second substantially cup-shaped configuration, said first and second line segments span a symmetry plane of said pad and of said medical dressing.

When the first and second line segments span a symmetry plane of said pad and of said medical dressing, the first and second portions of the medical dressing is identical. In addition, if the ratio between the length of the first line segment and the length of the second line segment is one, then the first end-points of the first and the second line segments are connected in the center of the medical dressing.

According to at least one example embodiment of the present invention said fixed connection of said first and second portions is provided by means of a welded seam. A welded seam fixedly connects the first portion and the second portion of the medical dressing without the need of excess material which may have been needed if the fixed connection would be achieved by sewing. Moreover, a welded seam may be smoother, and hence create less discomfort for the patient, than any other type of seam, which may connect the first and the second portion fixedly to each other. A welded seam may provide a strong fixed connection which is not easy to tear apart.

According to at least one example embodiment of the present invention the fixed connection of the first and second portion is provided by means of an adhesive. Such adhesive may for example be a melt adhesive.

According to at least one example embodiment of the present invention the medical dressing further comprises at least one gripping tab outwardly projecting from said border portion.

The gripping tab facilitates inspection of the skin or of the wound. The tab guides the caregiver to lift the dressing, inspect the skin underneath the dressing, and to thereafter re-apply the dressing onto the skin.

According to at least one example embodiment of the present invention, the gripping tab is made in one piece with the border portion. This is practical from a manufacturing perspective. However, other alternatives such as separate gripping tabs attached to the border portion are also conceivable.

According to at least one example embodiment of the present invention, the medical dressing may suitably be provided with more than one gripping tab. For instance, there may be two gripping tabs. According to at least one example embodiment of the present invention having at least two gripping tabs, a first tab may be located on one side of the symmetry plane and a second tab may be located on the other side of the symmetry plane. Such first and second tabs may be located symmetrically with respect to the symmetry plane of the medical dressing. According to another example embodiment having at least two gripping tabs, the first and the second tab may be located on the same side of the symmetry plane.

According to at least one example embodiment of the present invention there may be more than two gripping tabs, for instance three or four gripping tabs. Regardless of if one, two, three or four gripping tabs are present on a medical dressing according to embodiments of the invention, each gripping tab is suitably coplanar with the border portion and is suitably made in one piece with and projecting outwardly from the border portion. It should be understood that inwardly means a direction towards the pad, while outwardly is an opposite direction.

According to at least one example embodiment of the present invention, the one or more gripping tabs, is/are coated with an adhesive layer for adhering the tab to skin surrounding the area of prevention. This may be advantageous to avoid accidental removal forces being applied to the gripping tab/tabs, bearing in mind that a gripping tab is more likely to rise relative to the rest of the product if it is not adhered to the skin. The adhesive layer may be of the same type as described above for the adhesive layer of the adhesive body contact layer.

According to at least one example embodiment of the present invention the border portion has a tensile strength of between 3.5 and 10 N, preferably between 4 and 6 N at an elongation of 25%, as measured by ASTM D 882-12.

The tensile strength of the border portion is important for the ease of handling the border portion during nursing so that inspection of the skin can be performed easily. When the medical dressing is used for preventing pressure ulcers it is important that the caregiver can inspect the skin in order to discover any changes of the skin appearance which may be an early indication of a pressure ulcer that is about to develop. It may also be desirable to be able to inspect the skin or wound also for medical dressings for other uses than pressure ulcer prevention. As medical dressings may be expensive, it is desired that they can be detached and re-applied when inspections of the wound or skin are done. The border portion must therefore comprise certain rigidity. The rigidity must be sufficient so that the border portion does not curl or folds towards itself during inspection. On the other hand, the border portion should not be too rigid so that it does not follow and conform to a contoured surface of the skin. A tensile strength of 3.5-10 N has therefore been proven to be beneficial.

According to at least one example embodiment of the present invention, said border portion is formed by said adhesive body contact layer and a backing layer;

wherein said adhesive body contact layer and said backing layer each has an extension such that said pad is provided between said adhesive body contact layer and said backing layer; and wherein said adhesive body contact layer and said backing layer extend beyond the rim of said pad to define said border portion.

According to at least one exemplary embodiment, the backing layer may be a thin film, sheet, or membrane that is vapor permeable and waterproof. The backing layer is preferably made from a material that can reduce friction when a patient slides in bed. Examples of suitable materials for the backing layer include, but are not limited to, breathable polyurethane, polyester, polyethylene or polyamide films, silicone films, polyester-based nonwoven materials, and laminates of polyester-based nonwoven materials and polyurethane films. In at least some embodiments, the backing layer is co-extensive with the adhesive body contact layer in that both layers have the same outer dimensions. The backing layer may be bonded to the pad and/or the adhesive body contact layer, for example, via an adhesive such as a pressure sensitive adhesive. An example of a pressure sensitive adhesive is acrylic adhesive.

According to at least one example embodiment, the adhesive body contact layer comprises a film layer and an adhesive layer. By providing an adhesive layer covering the pad the adhesion to the skin is enhanced, and the medical dressing will thereby easier stay on the convex part of a human body. Since the medical dressing with an adhesive layer will attach better to the skin, the friction between the skin of the patient and the dressing surface is reduced, when a bedridden person slides or moves his heels in bed.

The adhesive layer can be considered to be provided on a body-facing proximal side of the body contact layer. If the border portion is formed by the adhesive body contact layer and a backing layer, then the backing layer is attached to the opposite distal side of the film of the body contact layer. It shall be understood that the proximal side being the side closest to the body when the medical dressing is in use. The adhesive body contact layer has been described above for the border portion, and the same features and specifications are valid also when the body contact layer also extends over one of the surfaces of the pad.

According to at least one example embodiment of the present invention said backing layer has a friction coefficient of less than 1.5 N, as measured by the test method ASTM D 1894-14.

The friction coefficient is preferably low such that the friction between the dressing and the bed sheet is reduced when a patient slides in bed. Reducing friction is an important aspect, since friction is a source of detrimental shear forces. The backing layer acts as a "sliding layer" and prevents translation of friction into harmful shear forces on the patient's skin.

According to at least one example embodiment of the present invention said fixed connection of said first and second portions is provided by means of a welded seam that extends through the adhesive body contact layer and the backing layer.

According to this exemplary embodiment, the welded seam extends through the two outer layers of the medical dressing when it is being used, i.e. the backing layer and the adhesive body contact layer. Depending on the configuration of the pad, i.e. whether it is provided with an indentation or not as described above, the welded seam may or may not extend through the pad.

According to at least one example embodiment of the present invention said adhesive body contact layer comprises an adhesive layer which covers at least 60% of the surface of the medical dressing, or more preferably at least 75% of the surface of the medical dressing and most preferably at least 90% of the surface of the medical dressing.

A greater coverage of adhesive on the surface of the pad aids in preventing undesirable friction forces which could form between the skin and the dressing as a patient slides in bed. Moreover, it is beneficial to have an even distribution of adhesive over the surface of the pad in order to keep the dressing in place during use.

The features and specifications described above for the adhesive body contact layer are also valid for this exemplary embodiment of the adhesive body contact layer.

According to at least one example embodiment of the present invention the medical dressing further comprises a release layer, intended to be removed before use. The release layer may be disposed on and releasably attached to the proximal side of the adhesive body contact layer. By "releasably attached," it is meant that the release layer may be peeled away from the rest of the medical dressing by hand. The release layer acts as a barrier that can protect the sterility of the pad and any adhesive (such as said adhesive layer) present on the proximal surface of the adhesive body contact layer (and any adhesive present on the backing layer and pad depending on their extension relative to the body contact layer) before the dressing is used. The release layer may be made of any of a variety of suitable materials known in the art, such as, for example, polyethylene, polyester, polypropylene, and silicone-coated paper.

According to at least one example embodiment of the present invention, said adhesive body contact layer comprises two sub-layers;

wherein a first sub-layer of said body contact layer comprises a polymer film; and wherein a second sub-layer of said body contact layer is an adhesive silicone layer.

According to at least one example embodiment, the adhesive body contact layer comprises a polymer film covered by an adhesive silicone layer. Suitable materials for the film include, but are not limited to breathable polyolefin based films (such as polyethylene), polyamide, polyester polyurethane, and silicone. A suitable material for use as the film is a thin polyurethane film. For example, the film of the body contact layer may be a polyurethane film having a thickness from 15 and 100 µm, e.g. from 40 to 80 µm, preferably from 45 to 60 µm.

The adhesive used should be skin-friendly and permit the removal of the dressing without causing damage to the skin. It should also have a strong adhesive effect to enable a prolonged time of use. Adhesive silicones fulfill these requirements. Examples of suitable silicone gels include two component RTV systems, such as Q72218 (Dow Corning), and SilGel 612 (Wacker Chemie AG), as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4. The thickness of the adhesive layer is preferably at least 20 µm.

According to at least one example embodiment of the present invention the adhesive layer may be perforated. The perforations typically extend through the whole body contact layer. The perforations allow for a quick absorption into the pad without compromising the tight fit to the skin provided by the adhesive layer, arranged to be in contact with the skin. The perforation allows the body exudates, such as wound fluids, or other moisture to be transported away from the skin.

According to at least one example embodiment of the present invention, the perforations may have different shapes and densities along varying regions of the body contact layer, and may be arranged in a regular or irregular pattern. Typically, the plurality of perforations is arranged in a predetermined, regular pattern. The perforations may have a diameter of from 0.5 mm to 10 mm, e.g. from 1 to 5 mm, e.g. from 1 to 2 mm. The total area of the perforations corresponds to the area of the medical dressing which is not covered by the adhesive layer.

According to at least another embodiment of the present invention the adhesive layer comprises an aperture. The aperture allows for quick absorption of body fluids into the pad.

According to at least one example embodiment of the present invention said pad comprises a first layer and a second layer; said first layer being arranged between said backing layer and said second layer of the pad, wherein said first layer has a higher affinity for liquid than said second layer.

This construction is believed to be beneficial when it comes to microclimate. Since the first layer has a higher affinity for moisture than the second layer, moisture will move to the first layer, and thereafter evaporate from the backing layer. This way, there will not be an accumulation of body fluids close to the skin, but the second layer may be kept relatively dry.

According to at least one example embodiment of the present invention the first layer comprises a superabsorbent material, such as for example superabsorbent fibers (SAF) or superabsorbent polymers (SAP). For example, polyacrylic super-absorbent fibers may be suitable. The first layer may also comprise binding fibers, non-limiting examples of which include polyester fibers, polyethylene fibers, polypropylene fibers, and blends thereof. Alternatively, or additionally, the first layer comprises an absorbent foam material. Alternatively, or additionally, the first layer may comprise cotton fibers.

According to at least one example embodiment of the present invention the second layer may act as a liquid acquisition layer and/or liquid distribution layer, and may be made of foams and/or cellulose based materials. It may for example be a hydrophilic foam such as hydrophilic polyurethane foam. In some embodiments, the second layer acts as a wicking or spreading layer and may comprise a non-woven material, e.g. viscose, polyester or blends thereof.

According to at least one example embodiment of the present invention the pad may comprise a third layer. The third layer may be provided between the first layer and the second layer. According to at least one example embodiment of the present invention the third layer is a liquid distributing layer, which can spread the liquid being absorbed by the second layer and transmit the liquid to the first layer. According to at least one example embodiment of the present invention, the third layer may comprise a non-woven material, such as, for example, viscose, polyester, or both.

According to at least one example embodiment of the invention the two or three layers of the pad may be laminated together.

According to at least one example embodiment of the present invention the pad comprises a material that yields a pressure-relieving effect.

According to a second aspect of the present invention a method for providing a medical dressing for a convex part of the human body is provided. Said method comprising:
    providing a medical dressing having a backing layer, a pad, an adhesive body contact layer and a release layer, wherein said pad is provided between said backing layer and said adhesive body contact layer, and said release layer is provided on said adhesive body contact layer;
    folding said medical dressing along a first line segment such that a first portion of the backing layer comes into contact with a second portion of the backing layer and wherein said release layer thereby becomes the outermost layer of the folded medical dressing;
    welding said medical dressing along a second line segment such that a welded seam is provided, wherein said welding is done through the backing layer, adhesive body contact layer and release layer, such that a first part of the backing layer and a first part of the adhesive body contact layer become fixedly connected to a second part of the backing layer and a second part of the adhesive body contact layer by means of said welded seam.

The effects and features of a medical dressing provided by means of the second aspect of the present invention are largely analogous to those described above in connection with the first aspect of the present invention. Embodiments of a medical dressing mentioned in relation to the first aspect of the present invention are possible to produce by means of a method according to the second aspect of the invention.

An advantage of providing a medical dressing according to the second aspect of the invention is that welding is done not only through the adhesive body contact layer and backing layer, but also through the release layer. Welding layers of a medical dressing in which an adhesive body contact layer is the outermost layer may be difficult as the adhesive layer may adhere to the welding equipment. By welding through the release layer, which covers the adhesive body contact layer, this risk is avoided. Another advantage of welding through the release layer is that the welding equipment does not need to come into direct contact with the adhesive body contact layer. The adhesive body contact layer is intended to be placed against a patient's skin when the medical dressing is being used. Hence, with the inventive method, the risk of contamination of a layer of the medical dressing that is intended to come into contact with the patient is also mitigated.

Welding a seam is also advantageous in that excess material of the backing layer and the adhesive body contact layer may be looseened and removed during the welding process. This provides for a medical dressing having a smooth adhesive body contact layer, which, as mentioned for other exemplary embodiments above, is advantageous in terms of reduced risk for discomfort and drawbacks for the patient. With excess material is meant to understand material of the backing layer and/or adhesive body contact layer that is provided further away from the pad than the welded seam.

According to an exemplary embodiment, the welding is performed by means of heat welding, ultrasound welding or radio frequency welding. Any one of these welding techniques have proven to be beneficial in welding a medical dressing and may therefore suitably be employed in a method according to a second aspect of the present invention.

According to an exemplary embodiment, at least a portion of said welded seam is provided adjacent at least a portion of said first line segment. Hence, according to this exemplary embodiment, at least one portion of each one of the first and second line segments are adjacent each other. It may for example be an end point of the respective line segments that are adjacent each other. With adjacent is meant that they are close to each other, but they do not need to be in contact with each other.

According to an exemplary embodiment, said welded seam is provided such that the medical dressing may be unfolded to a cup-shaped configuration in which the backing layer is the outermost layer of the medical dressing. Hence, according to this embodiment, the welded seam is provided such that the medical dressing may be unfolded, or turned inside out, from its state in which the release layer is the outermost layer. Thereby, after unfolding, the backing layer becomes the outermost layer of the medical dressing and the welded seam provides for a cup-shape of the medical dressing. This cup-shaped configuration is the intended use configuration of the medical dressing.

According to an exemplary embodiment, the pad of said medical dressing is provided with an indentation, and said welded seam is provided in said indentation. Providing an indentation in the pad, and providing the welded seam in said indentation has several advantages. One advantage is that by providing the pad with an indentation less material will be used for the pad and the risk for excess material gathering is reduced. Without having an indentation, material from the pad may be gathered for example under the heel when the medical dressing is in use. Such gathered material may cause the patient discomfort and may chafe the patient's skin. In other words, a smother inner surface of the medical dressing when arranged in the second substantially cup-shaped configuration may be provided when the pad comprises an indentation. Another advantage is that manufacturing is simplified when the welded seam does not have to be provided through the pad. Even if it is possible to provide a welded seam through certain types of pad materials, there is less limitations in choosing material for the pad if the welded seam instead is provided in the indentation.

The length of the indentation, and thereby the length of the welded seam affects the cup-shape of the medical dressing. Providing medical dressings with different lengths of the indentations may therefore be beneficial in order to provide medical dressings that fit different patients and different convex body parts.

According to at least one example embodiment the welded seam is provided such that the edges of the opposite sides of the indentation are brought closer to each other by the fixed connection. By bringing the opposite sides of the indentation closer together, the cup-shape of the medical dressing is formed. Furthermore, in this embodiment, also the width of the indentation affects the cup-shape of the medical dressing. Providing medical dressings with different widths of the indentations may therefore be beneficial in order to provide medical dressings that fit different patients and different convex body parts.

According to at least one example embodiment of the present invention said method further comprises providing said first and second line segments such that they are connected at a respective first end-point; and such that an angle between 90 and 175 degrees, or preferably between 120-170 degrees, or more preferably between 140-160 degrees, is formed between said first and second line segments.

Hence, according to this embodiment, the first and second line segments are connected to each other. The angle formed by the first and second line segments decides the depth of the cup when the medical dressing is in its cup-shaped configuration. For example, if the angle is closer to 175 degrees the cup will be shallower as compared with if the angle is closer to 90 degrees. It may be desirable to provide medical dressings with different angles, to provide different sizes of the cup such that it better fits different convex parts of human bodies such as, for example, a heel, an elbow, or a knee. Moreover, the size of the convex part may vary between different patients of the medical dressing.

According to at least one example embodiment of the present invention, said backing layer and said adhesive body contact layer extend beyond the rim of said pad to define a border portion of the medical dressing, wherein a respective second end point of the first and second line segments are distanced from each other and provided on a peripheral edge of said border portion. According to this embodiment, the first and second line segments are provided such that they extend from a respective point on the peripheral edge of the border portion of the medical dressing, and to some other point of the medical dressing that is either adjacent each other or in contact with each other. If the first and/or second line segment would not end at the peripheral edge of the border portion, portions of the medical dressing would not be connected to each other close to the border, and the risk for gaps, wrinkles or folds of the medical dressing when applied to a patient would then be higher.

According to a third aspect of the present invention a medical dressing is provided. The medical dressing comprises:
  a pad
  an adhesive body contact layer
  a backing layer
  a border portion extending along the contour of the pad, the border portion forming a peripheral edge of said medical dressing,
  said adhesive body contact layer or said backing layer comprising a first and a second portion;
  wherein said pad is provided between said body contact layer and said backing layer;
  wherein said first and second portions are provided on different sides of a first imaginary straight line which extends along the adhesive body contact layer or the backing layer from one peripheral edge of said adhesive body contact layer or said backing layer to an opposite peripheral edge of said body contact layer or said backing layer; and
  wherein said first and second portions are provided on the same side of a second imaginary line which extends along the body contact layer or the backing layer from one peripheral edge of the medical dressing to an opposite peripheral edge of said medical dressing in a direction perpendicular to said first line; and
  wherein said medical dressing is provided such that said first portion of said adhesive body contact layer is connected to said second portion of said adhesive body contact layer by means of a fixed connection; and
  wherein said medical dressing is provided such that said first portion of said backing layer is fixedly connected to said second portion of said backing layer.

The effects and features of a medical dressing provided by means of the third aspect of the present invention are analogous to those described above in connection with the first and second aspects of the present inovation. Embodiments mentioned in relation to the first and second aspects of the present invention are compatible with the third aspect of the invention.

According to at least one example embodiment of the present invention said body contact layer and said backing layer extend beyond the rim of said pad to define said border portion which extends along the contour of said pad. Hence, the surface area of the body contact layer and the backing layer is larger than the surface area of the pad.

According to at least one example embodiment of the present invention the first line crosses the second line at a distance which corresponds to 30-50%, more preferably 40-50%, and most preferably 50% of the length of said second line from one peripheral edge; and wherein said second line crosses the first line at a distance which corresponds to 30-50%, more preferably 40-50%, and most preferably 50% of the length of said first line from one peripheral edge. When the first line crosses the second line at a distance which corresponds 50% of the length of the second line and vice versa the first and second line crosses in the center of the medical dressing. By providing medical dressings where the first line crosses the second line at varying distances of the second line or vice versa, different cup-shapes can be achieve which can be used for different convex parts of a human body and/or of different patients.

BRIEF DESCRIPTION OF THE DRAWINGS

The above objects, as well as additional objects, features and advantages of the present invention, will be more fully appreciated by reference to the following illustrative and non-limiting detailed description of preferred embodiments of the present invention, when taken in conjunction with the accompanying drawings, wherein.

DETAILED DESCRIPTION OF THE DRAWINGS

In the present detailed description, embodiments of the present invention will be discussed in relation to the accompanying figures. It should be noted that this by no means limits the scope of the invention, which is also applicable in other circumstances for instance with other types or variants of medical dressings than the embodiments shown in the appended drawings. Further, that specific features are mentioned in connection to an embodiment of the invention does not mean that those components cannot be used to an advantage together with other embodiments of the invention.

Figure 1:
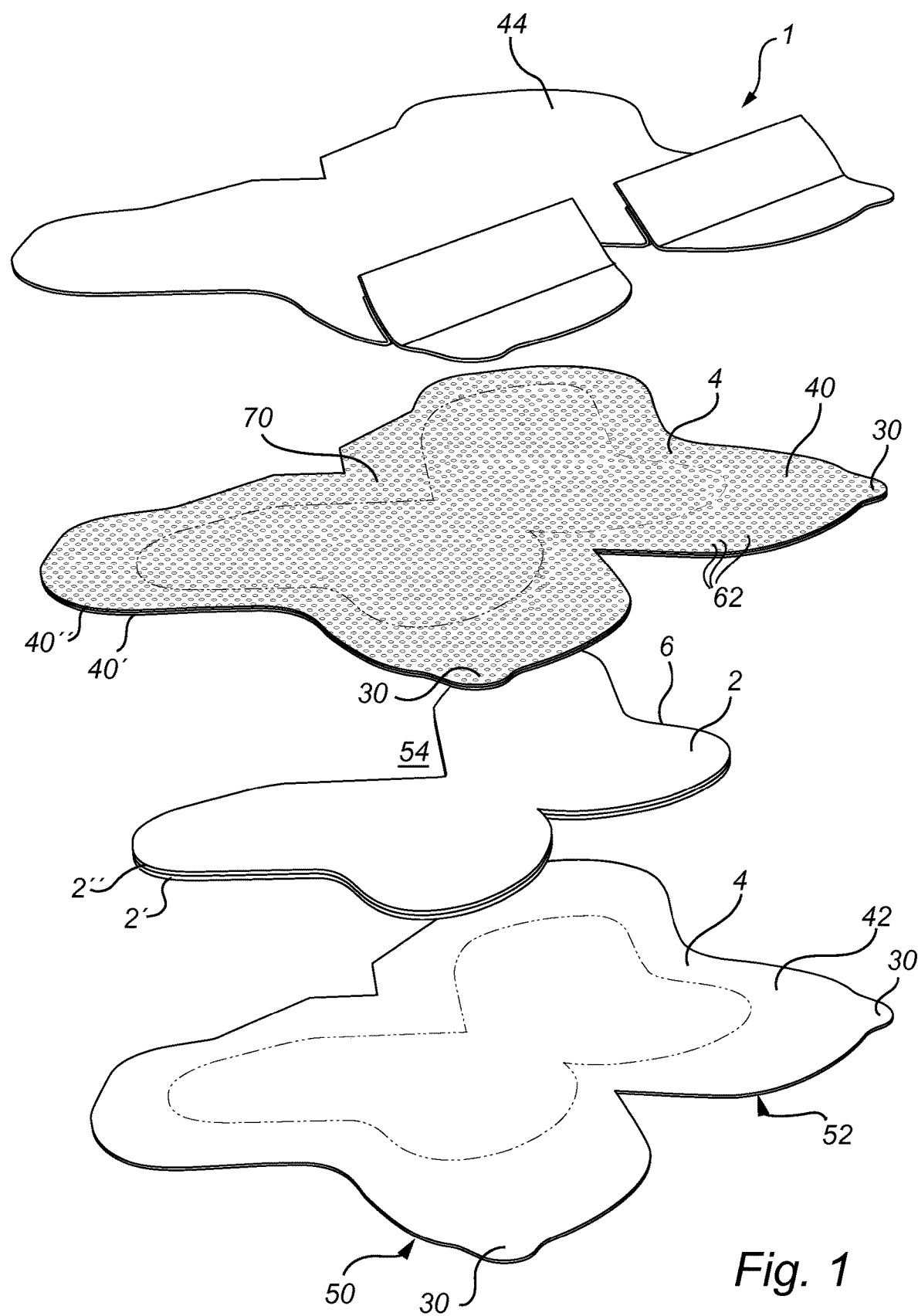
FIG. 1 shows an exploded view of a medical dressing in accordance with at least one example embodiment of the invention.

FIG. 1 shows an exploded view of a medical dressing 1 for use on a convex part of a human body. The exploded view visualizes in which order the different layers of the medical dressing is arranged. Starting from the bottom of FIG. 1, the first layer is the backing layer 42. On top of the backing layer 42 the pad 2 is arranged and on top of the pad 2 the adhesive body contact layer 40 is provided. Hence, the pad 2 is provided between the adhesive body contact layer 40 and the backing layer 42. The top layer of FIG. 1 is the release layer 44.

The pad 2 comprises a rim 6. Further, the pad 2 comprises a first 2' and a second layer 2". The first layer 2' of the pad 2 has a higher liquid affinity of than the second layer 2". The first layer 2' is the bottom layer of the pad 2 in FIG. 1. Hence, the first layer 2' is arranged between the second layer 2" of the pad 2 and the backing layer 42. As seen in FIG. 1 the pad is provided with an indentation 54.

The first layer 2' may comprise a superabsorbent material, such as for example superabsorbent fibers (SAF) or superabsorbent polymers (SAP).

The second layer 2" may act as a liquid acquisition layer and/or liquid distribution layer, and may be made of foams and/or cellulose based materials. In some embodiments, the second layer 2" acts as a wicking or spreading layer and may comprise a nonwoven material, e.g. viscose, polyester or blends thereof.

The adhesive body contact layer 40 comprises a first 40' and a second sub-layer 40". The first sub-layer 40' of the adhesive body contact layer 40, being the bottom sub-layer of the adhesive body contact layer 40 in FIG. 1, comprises a polymer film.

The adhesive layer 40" may be perforated. In the illustrated embodiment, the perforations are evenly distributed over the entire surface of the adhesive body contact layer 40. The perforations 62 typically extend through the whole adhesive body contact layer 40. The perforations 62 allow for a quick absorption into the pad without compromising the tight fit to the skin provided by the adhesive layer, arranged to be in contact with the skin. The perforations 62 allows the body exudates, such as wound fluids, or other moisture to be transported away from the skin.

The backing layer 42 is co-extensive with the adhesive body contact layer 40 in that both layers have the same outer dimensions. The surface area of the backing layer 42 and the adhesive body contact layer 40 is larger than the surface area of the pad 2. Hence, the backing layer 42 and the adhesive body contact layer 40 will extend outside the rim 6 of the pad 2 forming a border portion 4. The border portion 4 extends along said rim 6 (in this illustrated embodiment along the entire rim 6). The border portion 4 following the edges of the indentation 54 will later be referred to as excess material 70. The surface area of the pad 2 is marked with a dash-dotted line on both the backing layer 42 and the adhesive body contact layer 40. Both the backing layer 42 and the adhesive body contact layer 40 comprises gripping tabs 30 which are outwardly projecting parts of the border portion 4. In FIG. 1 there are two gripping tabs 30 on each layer. The release layer 44 is provided to protect the adhesive surface of the adhesive body contact layer and will be removed before use of the medical dressing 1.

When the product is to be assembled, the backing layer 42 may be bonded to the pad 2 and/or the adhesive body contact layer 40, for example, via an adhesive such as a pressure sensitive adhesive.

Figure 2:
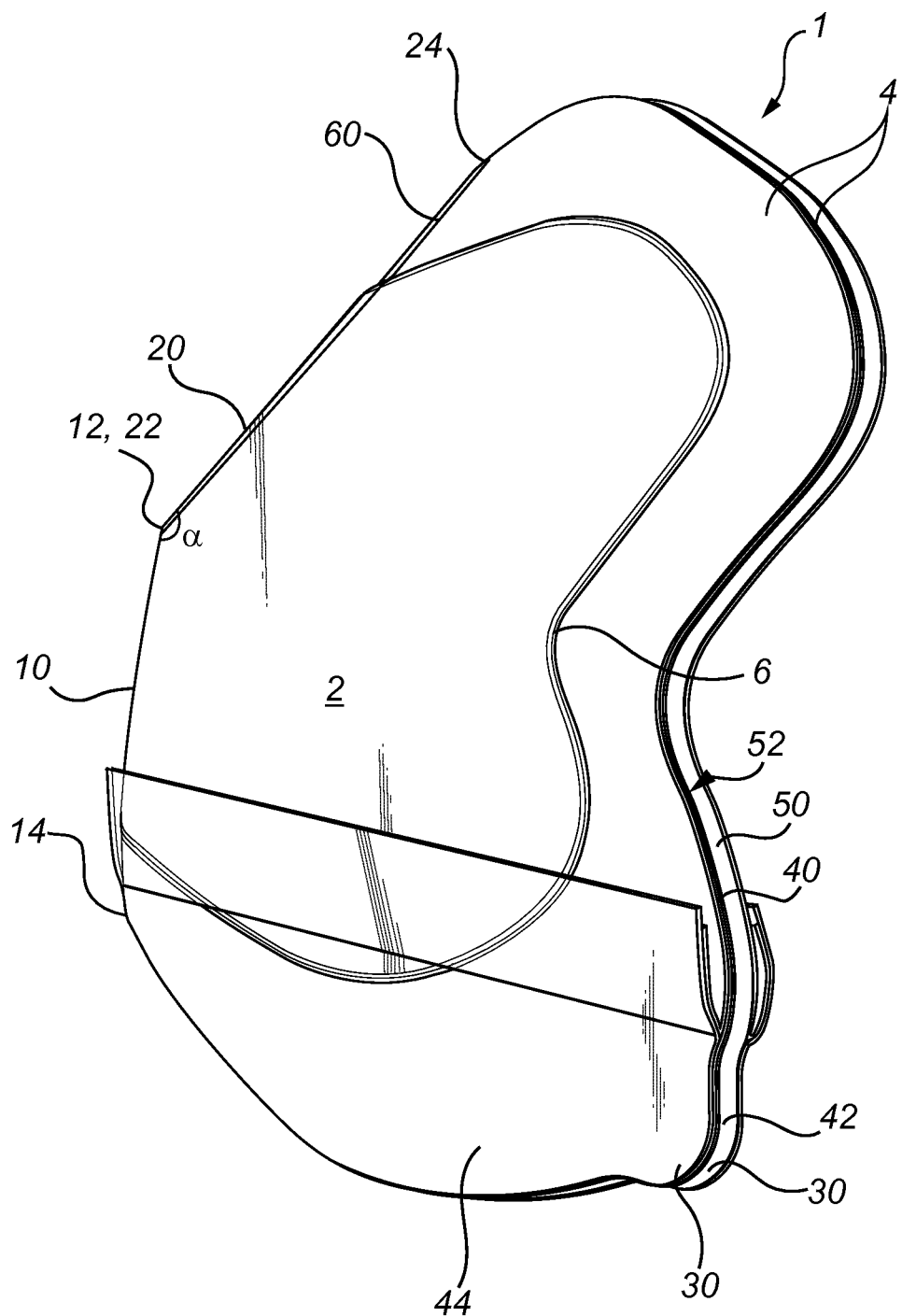
FIG. 2 shows a schematic, perspective view of the medical dressing of FIG. 1 in a first substantially planar configuration.
Figure 3:
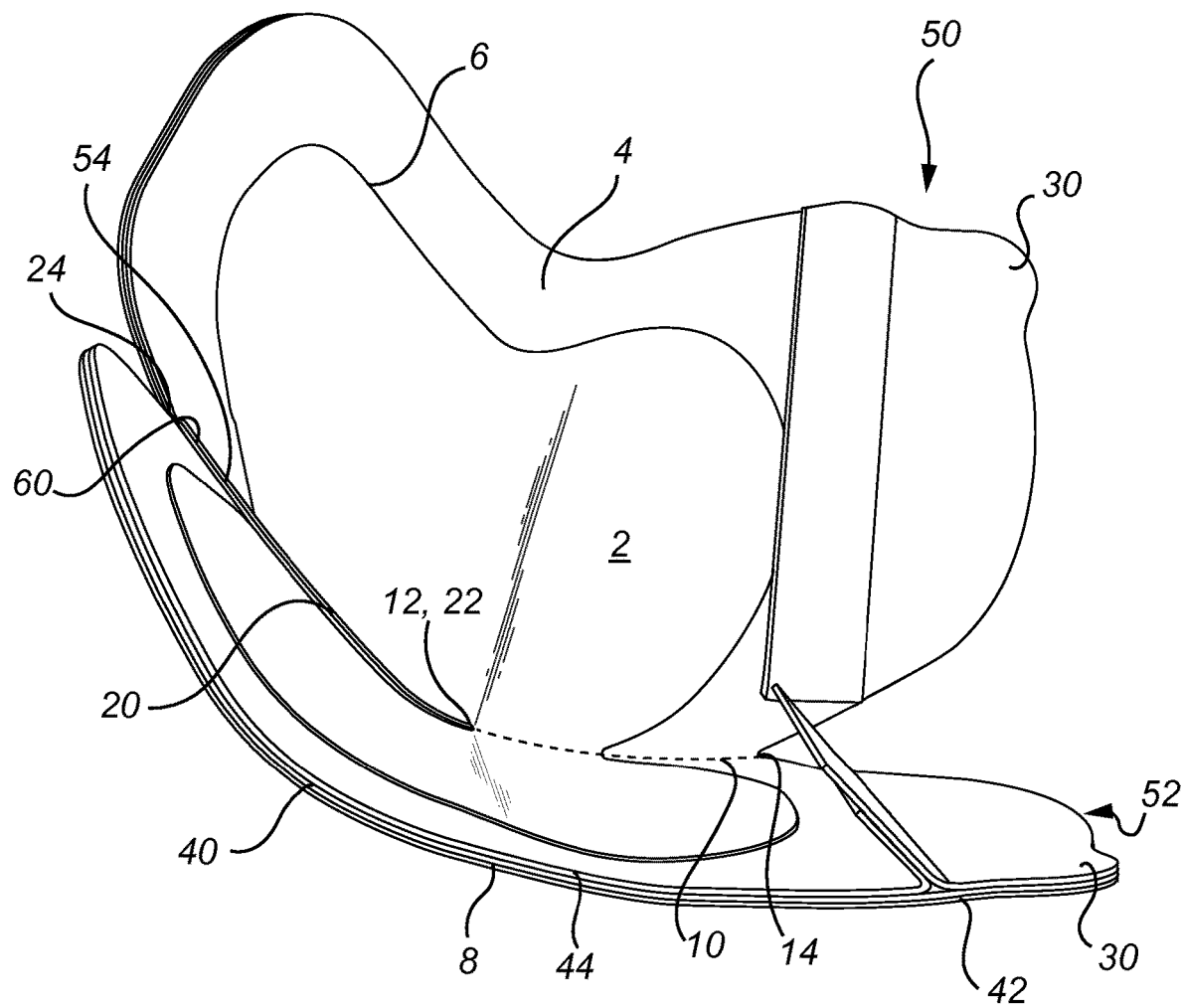
FIG. 3 shows a schematic, perspective view of the medical dressing of FIGS. 1-2 in a second substantially cup-shaped configuration.

Now turning to FIGS. 2 and 3, which show the medical dressing 1 when arranged in a first substantially planar configuration (FIG. 2) and a second substantially cup-shaped configuration (FIG. 3). The second substantially cup-shaped configuration is the preferred configuration of use of the medical dressing whereas the first substantially planar configuration may be used e.g. for production, transportation and storage of the medical dressing 1.

In the first substantially planar configuration of the medical dressing, the backing layer 42 is turned inwards whereas the release layer 44 is turned outwards and forms the outermost layer of the medical dressing. The medical dressing 1 is folded along a first line defining a first line segment 10 having a first 12 and a second end point 14 such that a first portion 50 of said medical dressing is facing a second portion 52 of said medical dressing. Hence, the first portion 50 and the second portion 52 of the medical dressing 1 is integral with each other and connected along the folded line segment. In the first substantially planar configuration, the first portion 50 and the second portion 52 are contacting each other and therefore only a small part of one of them are visible in FIG. 2. In this embodiment, it is the backing layer 42 that is in contact with another part of the backing layer 42. In other words, the medical dressing 1 has, when in its first substantially planar configuration, its inside out.

The first 50 and second 52 portions of said medical dressing are also connected to each other by means of a fixed connection 60 along a second line defining a second line segment 20 having a first 22 and a second end-point 24. The fixed connection 60 is provided in the indentation 54 such that the rims 6 of the pad 2 on both sides of the indentation 54 are brought closer together and such that the rims 6 of the pad 2 on both sides of the indentation 54 are contacting each other. The first 10 and second line segments 20 are connected at their respective first end-points 12, 22 such that an angle α between 90 and 175 degrees is formed between the first 10 and the second line segments 20 of the medical dressing. The size of the angle affects the shape of the cup; a bigger angle correlates to a shallower cup. In FIG. 2 the angle α is 145 degrees. The fixed connection 60 is in the illustrated embodiment a welded seam that extends through the adhesive body contact layer 40, and the backing layer 42.

FIG. 3 shows the medical dressing 1 for use on a convex part of the human body arranged in the second substantially cup-shaped configuration. The border portion 4 extends along the rim 6 of the pad 2 such that the border portion 4 is forming a peripheral edge 8 of said medical dressing 1. The second end-points 14, 24 of the first 10 and second line segments 20, respectively, lays on the peripheral edge 8 of said medical dressing 1. The first line segment 10 is here shown as a dashed line. In the second substantially cup-shaped configuration, the first 10 and second line segments 20 span a symmetry plane of the pad 2 and of said medical dressing 1, such that the first portion 50 and the second portion 52 of the medical dressing 1 are identical to each other.

The medical dressing 1 will now be described in use, with reference to FIGS. 2, 3, 4a and 4b. The medical dressing 1 is usually stored and transported in its first substantially planar configuration as shown in FIG. 2, i.e. it will be stored with its inside out. Storing it in its substantially planar configuration is beneficial in terms of e.g. space efficiency. When the medical dressing is to be applied to a patient, the person who will apply the medical dressing to the convex body part will put one hand inside the folded medical dressing 1, i.e. come into contact with the backing layer 42. Subsequently, the person removes the release layer 44 with his or her other hand. After removal of the release layer, the adhesive body contact layer 40 will be the outermost layer of the medical dressing 1. The medical dressing 1 will be placed such that the adhesive body contact layer contacts, i.e. is in physical contact with, the convex body part. It may for example be placed such that the bottom of the cup is placed towards the most protruding part of a heel or any other convex body part. From this position the medical dressing 1 will now be turned over to its second substantially cup-shaped configuration. The pad 2 on both sides of the second line segment 20, i.e. the fixed connection 60, is smoothed onto the skin. The border portion 4 following the rim 6 of the pad 2 on both sides of the second line segment, i.e. the fixed connection, is applied to the skin and is also smoothed in different directions in order to avoid or reduce the number of wrinkles. Subsequently, the pad 2 on both side of the first line segment 10 is arranged such that the size of the cup is fitted to the size of the convex body part, i.e. the cup-size is adapted to the patient. The pad 2 on both sides of the first line segment 10, i.e. the fold, is thereafter smoothed onto the skin. The border portion 4 following the rim 6 of the pad 2 on both sides of the second line segment 20 is then applied to the skin in the same manner as described above. By applying the medical dressing 1 as described above, there is no need for touching the adhesive side of the adhesive body contact layer 40 or the patient's skin during the application.

Figure 4A:
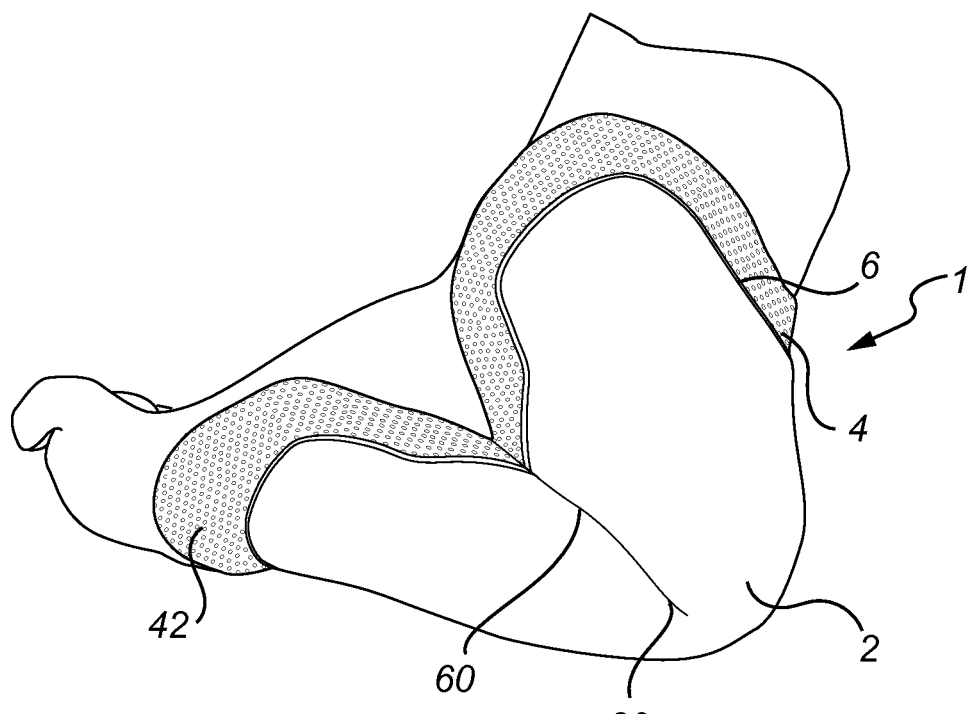
FIGS. 4a and 4b show a schematic, perspective view of the medical dressing of FIGS. 1-3, in use, provided on a heel.
Figure 4B:
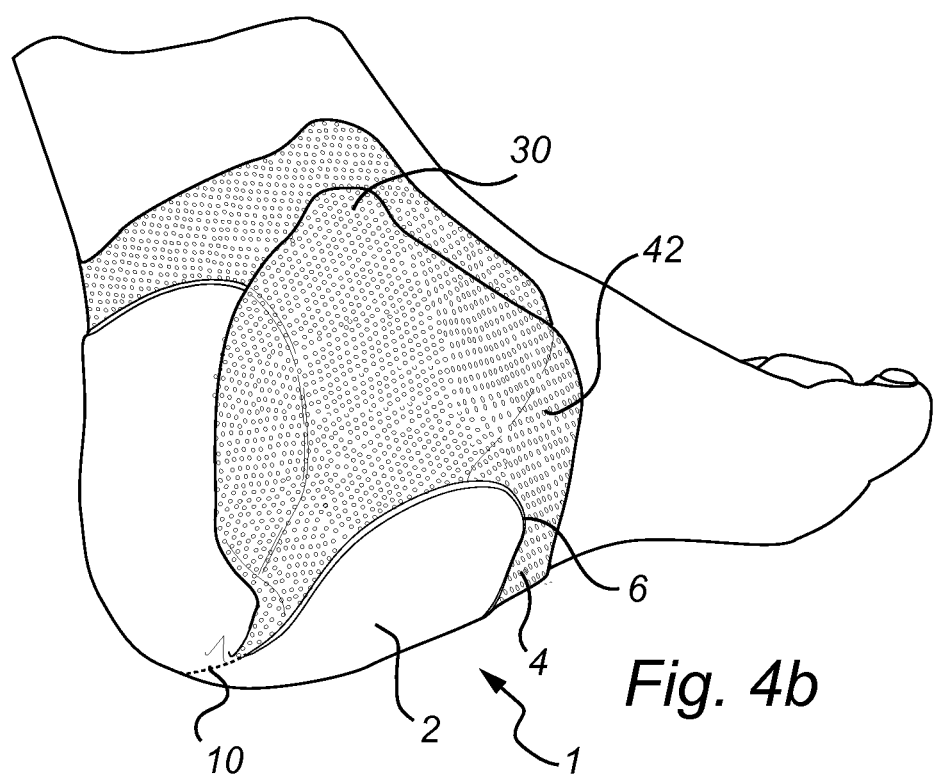

FIGS. 4a and 4b show the medical dressing 1 when it has been applied to a patient. Here, the medical dressing 1 is provided on a heel. FIG. 4a shows the outside of the foot and FIG. 4b shows the inside of the foot. When a bedridden patient lays in bed, it is common that the foot will fall such that the outside of the foot moves and lays towards the bed and therefore this part, i.e the outside of the heel, and also the malleoli, is a "high-risk-area" for pressure ulcer development. Hence, it is of importance that this area is covered by a whole cup and that there are no gaps in the medical dressing 1 in this area. Therefore, it is illustrated in FIGS. 4a and 4b that the cup of the second cup-shaped configuration of the medical dressing 1 is provided such that it follows the contour of the heel and such that the fixed connection 60, i.e. the second line segment 20, is arranged on the outside of the foot. The medical dressing has been applied to the foot in the manner described above for FIG. 3. In FIG. 4b it can be seen how the medical dressing 1 has been adapted to fit the patient. The border portion 4 is overlapping both itself and the pad 2. Moreover, the gripping tabs 30 project outwards from the border portion 4 to provide an indication where to release the medical dressing 1 from the skin for skin inspection. This portion of the dressing; i.e. the dressing portion defined by the first line segment 10 can be adjusted to fit feet of various sizes.

Foots of some patients may however have the tendency of falling inwards, instead of outwards, when the patient lays in bed. In such cases the medical dressing 1 can be applied such that the fixed connection 60 is arranged on the inside of the foot instead. The same medical dressing 1 can be used for both cases.

Figure 5:
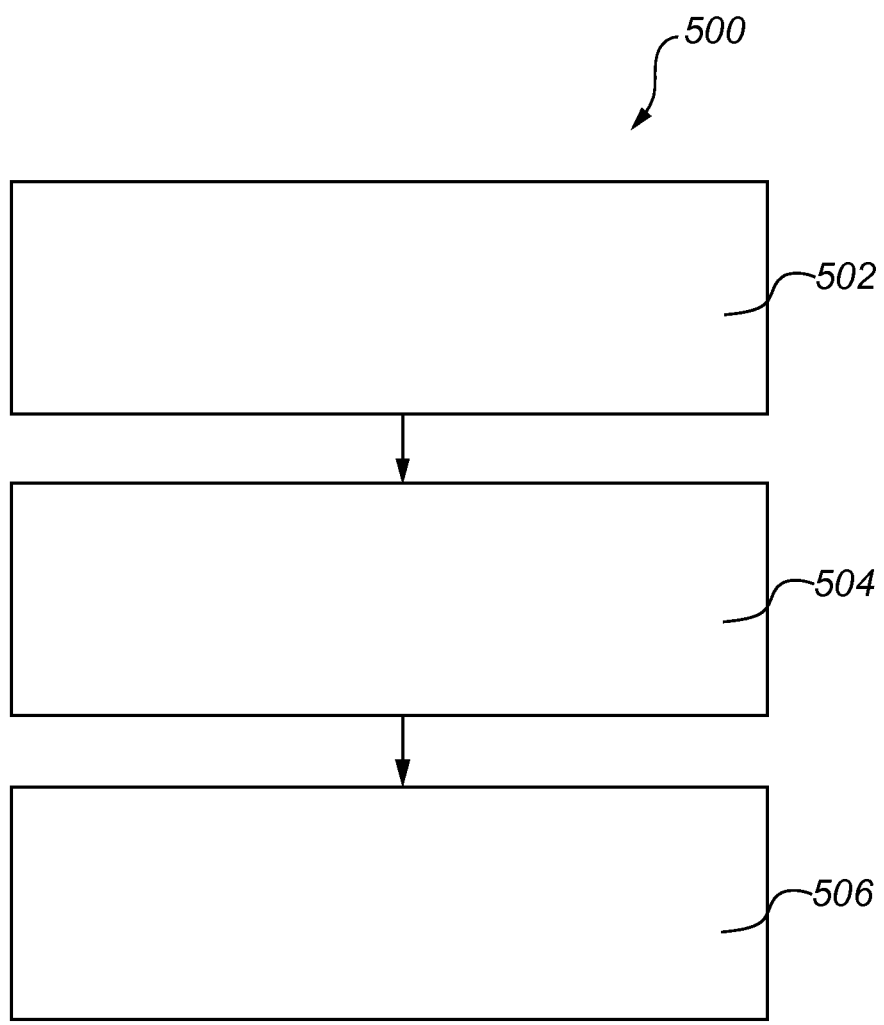
FIG. 5 shows a schematic view of a method for providing a medical dressing in accordance with at least one embodiment of the invention.

FIG. 5 schematically shows a method 500 for providing a medical dressing for a convex part of the human body. The method as described below may be used for producing the medical dressing of FIGS. 1-4.

The first step of the method 500 is to provide 502 a medical dressing having a backing layer 42, a pad 2, an adhesive body contact layer 40 and a release layer 44. The pad 2 is arranged between the backing layer 42 and the adhesive body contact layer 44. The release layer is provided to cover the adhesive side of the adhesive body contact layer 40. The medical dressing provided in this step is a flat medical dressing. Subsequently, the medical dressing will be folded 504 along a first line such that a first portion of said backing layer is facing and contacting a second portion of said backing layer. Hence, the outermost layer of the medical dressing will be the release layer. In other words, the medical dressing will be folded with its inside out. The fold defines a first line segment 10 having a first 12 and a second 14 end-point. As a next step of the method 506 the medical dressing is welded along a second line segment such that a welded seam 60 is provided. The welding is made through the backing layer 42, the adhesive body contact layer 40 and the release layer 44.

The first 10 and the second 20 line segments comprises a respective first end-point 12, 22 and a respective second end-point 14, 24. The first and the second line segments are provided such that they are connected in their respective first end-points 12, 22.

Figure 6:
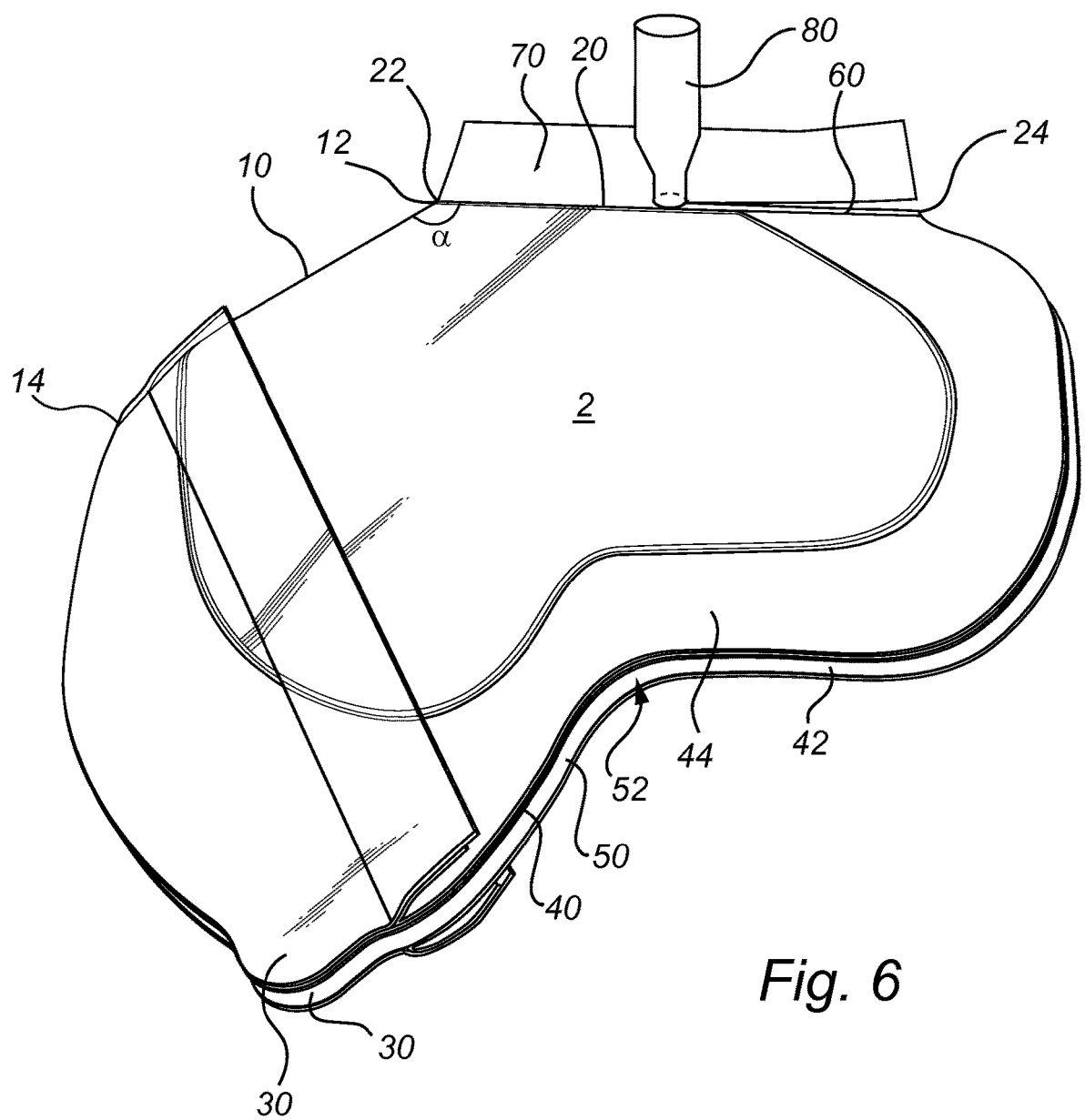
FIG. 6 shows a schematic view of the medical dressing of FIGS. 1-4 during production.

FIG. 6 shows the medical dressing of FIG. 1-4 during the step 506 as described in FIG. 5, i.e. during the welding of the folded medical dressing 1 along a second line. The welding is performed with welding equipment 80, for example heat welding, ultrasound welding or radio frequency welding. The welding equipment 80 is schematically shown in FIG. 6. The medical dressing 1 is arranged as in FIG. 2, i.e. in its first substantially planar configuration.

The welding will be made through the border portion 4 extending along the edges of the indentation 54 of the pad 2. The welding brings the edges of the pad 2 on both sides of the indentation 54 close together. By bringing the opposite sides of the indentation closer together, the cup-shape of the medical dressing is formed. Preferably, the welding is performed as close to the rim of the pad 2 as possible in the indentation. The welding will be made through the backing layer 42, the adhesive body contact layer and the release layer 44.

The welding will result in a welded seam which fixedly connects the first portion 50 to the second portion 52 of the medical dressing 1. Hence, in the illustrated embodiment, the welded seam is the fixed connection 60. During welding, excess material 70 will simultaneously be removed as seen in FIG. 6. It shall be understood that with excess material 70 is meant the backing layer 42 and/or adhesive body contact layer 40 that is provided further away from the pad 2 than the welded seam. In other words, it is material of the border portion 4 that would have been provided on the outside of the welded seam 60 if it is not removed. By removing this excess material 70 a smooth inner surface of the medical dressing 1 in its second, substantially cup-shaped configuration is provided.

The skilled person realizes that several modifications of the embodiments described herein are possible without departing from the scope of the invention, which is defined in the appended claims. For instance, the angle formed between the first and the second line segments may be altered to differentiate the depth of the "cup" for enable the use of the medical dressing to other convex parts of a human body, for example an elbow or a knee.

The invention claimed is:

1. A medical dressing for use on a convex part of the human body, said medical dressing comprises a pad and a border portion;
   wherein said pad comprises a rim and said border portion extends along said rim and comprises an adhesive body contact layer; and
   wherein said medical dressing can be arranged in a first substantially planar configuration and a second substantially cup-shaped configuration;
   wherein in said first substantially planar configuration:
      said medical dressing is folded along a first line defining a first line segment having a first and a second end-point such that a first portion and a second portion of said medical dressing is formed, wherein said first portion of said medical dressing is facing and contacting said second portion of said medical dressing;
      said first and second portions of said medical dressing are connected by means of a fixed connection along a second line defining a second line segment having a first and a second end-point;
      said first and second line segments being connected at their respective first end-points such that an angle between 90 and 175 degrees is formed between said first and second line segments;
   wherein in said second substantially cup-shaped configuration:
      said border portion forms a peripheral edge of said medical dressing; and
      said second end-points of said first and second line segments lay on said peripheral edge of said medical dressing,
   wherein said border portion is formed by said adhesive body contact layer and a backing layer;
   wherein said adhesive body contact layer and said backing layer each has an extension such that said pad is provided between said adhesive body contact layer and said backing layer; and
   wherein said adhesive body contact layer and said backing layer extend beyond the rim of said pad to define said border portion.

2. The medical dressing according to claim 1, wherein said pad comprises an indentation, and wherein said fixed connection of the medical dressing is provided in said indentation.

3. The medical dressing according to claim 1, wherein the ratio of the length of said first line segment and the length of said second line segment is 0.30-1.5.

4. The medical dressing according to claim 1, wherein in said second substantially cup-shaped configuration, said first and second line segments span a symmetry plane of said pad and of said medical dressing.

5. The medical dressing according to claim 1, wherein said fixed connection of said first and second portions is provided by means of a welded seam.

6. The medical dressing according to claim 1, wherein said medical dressing further comprises at least one gripping tab outwardly projecting from said border portion.

7. The medical dressing according to claim 1, wherein said border portion has a tensile strength of between 3.5 and 10 N at an elongation of 25%, as measured by ASTM D 882-12.

8. The medical dressing according to claim 1, wherein said backing layer has a friction coefficient of less than 1.5 N, as measured by the test method ASTM D 1894-14.

9. The medical dressing according to claim 1, wherein said fixed connection of said first and second portions is provided by means of a welded seam that extends through the adhesive body contact layer and the backing layer.

10. The medical dressing according to claim 1, wherein said adhesive body contact layer comprises an adhesive layer which covers at least 60% of the surface of the medical dressing.

11. The medical dressing according to claim 1, wherein said adhesive body contact layer comprises two sub-layers;
   wherein a first sub-layer of said body contact layer comprises a polymer film; and
   wherein a second sub-layer of said body contact layer is an adhesive silicone layer.

12. A method for providing a medical dressing for a convex part of the human body, said method comprising:
   providing a medical dressing having a backing layer, a pad, an adhesive body contact layer and a release layer, wherein said pad is provided between said backing layer and said adhesive body contact layer, and said release layer is provided on said adhesive body contact layer;

folding said medical dressing along a first line segment such that a first portion of the backing layer comes into contact with a second portion of the backing layer and wherein said release layer thereby becomes the outermost layer of the folded medical dressing;

welding said medical dressing along a second line segment such that a welded seam is provided, wherein said welding is done through the backing layer, adhesive body contact layer and release layer, such that a first part of the backing layer and a first part of the adhesive body contact layer become fixedly connected to a second part of the backing layer and a second part of the adhesive body contact layer by means of said welded seam.

13. A method for providing a medical dressing for a convex part of the human body according to claim 12, said method further comprising:

providing said first and second line segments such that they are connected at a respective first end-point; and such that an angle between 90 and 175 degrees is formed between said first and second line segments.

14. A method for providing a medical dressing for a convex part of the human body according to claim 12, wherein said backing layer and said adhesive body contact layer extend beyond the rim of said pad to define a border portion of the medical dressing, wherein a respective second end point of the first and second line segments are distanced from each other and provided on a peripheral edge of said border portion.

15. A medical dressing for use on a convex part of the human body, said medical dressing comprises a pad and a border portion;

wherein said pad comprises a rim and said border portion extends along said rim and comprises an adhesive body contact layer; and wherein said medical dressing can be arranged in a first substantially planar configuration and a second substantially cup-shaped configuration;

wherein in said first substantially planar configuration:

said medical dressing is folded along a first line defining a first line segment having a first and a second end-point such that a first portion and a second portion of said medical dressing is formed, wherein said first portion of said medical dressing is facing and contacting said second portion of said medical dressing;

said first and second portions of said medical dressing are connected by means of a fixed connection along a second line defining a second line segment having a first and a second end-point;

said first and second line segments being connected at their respective first end-points such that an angle between 90 and 175 degrees is formed between said first and second line segments;

wherein in said second substantially cup-shaped configuration:

said border portion forms a peripheral edge of said medical dressing; and said second end-points of said first and second line segments lay on said peripheral edge of said medical dressing, wherein said border portion is formed by said adhesive body contact layer and a backing layer, wherein said fixed connection of said first and second portions is provided by means of a welded seam that extends through the adhesive body contact layer and the backing layer.

* * * * *